(12) United States Patent
Moffitt et al.

(10) Patent No.: US 8,145,304 B2
(45) Date of Patent: Mar. 27, 2012

(54) NEURAL STIMULATION SYSTEM FOR CARDIAC FAT PADS

(75) Inventors: Julia Moffitt, Iowa City, IA (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 50 days.

(21) Appl. No.: 12/836,802

(22) Filed: Jul. 15, 2010

(65) Prior Publication Data

US 2010/0305634 A1    Dec. 2, 2010

Related U.S. Application Data

(62) Division of application No. 11/077,583, filed on Mar. 11, 2005, now Pat. No. 7,769,446.

(51) Int. Cl.
*A61N 1/08* (2006.01)

(52) U.S. Cl. .......................................................... 607/9

(58) Field of Classification Search ....................... 607/9
See application file for complete search history.

(56) References Cited

U.S. PATENT DOCUMENTS

| | | | |
|---|---|---|---|
| 5,243,980 A | 9/1993 | Mehra | |
| 5,334,221 A | 8/1994 | Bardy | |
| 5,356,425 A | 10/1994 | Bardy et al. | |
| 5,411,531 A | 5/1995 | Hill et al. | |
| 5,507,784 A | 4/1996 | Hill et al. | |
| 5,916,239 A | 6/1999 | Geddes et al. | |
| 6,725,093 B1* | 4/2004 | Ben-Haim et al. | ............. 607/9 |
| 7,123,961 B1 | 10/2006 | Kroll et al. | |
| 7,277,761 B2 | 10/2007 | Shelchuk | |
| 7,769,446 B2 | 8/2010 | Moffitt et al. | |
| 2003/0045909 A1 | 3/2003 | Gross et al. | |
| 2003/0229380 A1 | 12/2003 | Adams et al. | |
| 2004/0172075 A1 | 9/2004 | Shafer et al. | |
| 2004/0199210 A1* | 10/2004 | Shelchuk | .................. 607/17 |
| 2005/0096705 A1 | 5/2005 | Pastore et al. | |
| 2005/0149155 A1 | 7/2005 | Scheiner et al. | |
| 2005/0149156 A1 | 7/2005 | Libbus et al. | |

(Continued)

FOREIGN PATENT DOCUMENTS

EP    1304135 A2    4/2003

(Continued)

OTHER PUBLICATIONS

"European Application Serial No. 06737115.3, Office Action mailed Sep. 15, 2010", 4 pgs.

(Continued)

*Primary Examiner* — Eric D. Bertram
(74) *Attorney, Agent, or Firm* — Schwegman, Lundberg & Woessner, P.A.

(57) ABSTRACT

Various aspects relate to a device which, in various embodiments, comprises a header, a neural stimulator, a detector and a controller. The header includes at least one port to connect to at least one lead, and includes first and second channels for use to provide neural stimulation to first and second neural stimulation sites for a heart. The controller is connected to the detector and the neural stimulator to selectively deliver a therapy based on the feedback signal. A first therapy signal is delivered to the first neural stimulation site to selectively control contractility and a second therapy signal is delivered to the second neural stimulation site to selectively control one of a sinus rate and an AV conduction. Other aspects and embodiments are provided herein.

23 Claims, 7 Drawing Sheets

U.S. PATENT DOCUMENTS

| | | |
|---|---|---|
| 2005/0187584 A1 | 8/2005 | Denker et al. |
| 2005/0261741 A1 | 11/2005 | Libbus et al. |
| 2006/0079945 A1 | 4/2006 | Libbus |
| 2006/0106428 A1 | 5/2006 | Libbus et al. |
| 2006/0106429 A1 | 5/2006 | Libbus et al. |
| 2006/0206153 A1 | 9/2006 | Libbus et al. |
| 2006/0206154 A1 | 9/2006 | Moffitt et al. |
| 2006/0206159 A1 | 9/2006 | Moffitt et al. |

FOREIGN PATENT DOCUMENTS

| | | |
|---|---|---|
| WO | WO-03011388 A2 | 2/2003 |
| WO | WO-2005113066 A1 | 12/2005 |
| WO | WO-2006098928 A1 | 9/2006 |
| WO | WO-2006098996 A1 | 9/2006 |

OTHER PUBLICATIONS

"European Application Serial No. 06737115.3, Response filed Jan. 24, 2011 to Office Action mailed Sep. 15, 2010", 16 pgs.

"U.S. Appl. No. 11/077,583, Advisory Action mailed Aug. 22, 2007", 4 pgs.

"U.S. Appl. No. 11/077,583, Final Office Action mailed May 2, 2007", 8 pgs.

"U.S. Appl. No. 11/077,583, Non Final Office Action mailed Nov. 8, 2006", 7 pgs.

"Application Serial No. 11/077, Non-Final Office Action mailed Feb. 28, 2008", 8 pgs.

"U.S. Appl. No. 11/077,583, Response filed Jan. 14, 2008 to Restriction Requirement mailed Dec. 12, 2007", 10 pgs.

"U.S. Appl. No. 11/077,583, Response filed Feb. 8, 2007 to Non Final Office Action mailed Feb. 8, 2007", 14 pgs.

"U.S. Appl. No. 11/077,583, Response filed Jul. 2, 2007 to Final Office Action mailed May 2, 2007", 15 pgs.

"U.S. Appl. No. 11/077,583, Restriction Requirement mailed Dec. 12, 2007", 6 pgs.

"U.S. Appl. No. 11/077,583, Response filed Dec. 8, 2008 to Final Office Action mailed Oct. 6, 2008", 15 pgs.

"U.S. Appl. No. 11/077,583, Response filed Jun. 30, 2008 to Non-Final Office Action mailed Feb. 28, 2008", 11 pgs.

"U.S. Appl. No. 11/077,583, Response filed Sep. 28, 2007 to Final Office Action mailed May 2, 2007", 13 pgs.

"U.S. Appl. No. 11/077,583, Non-Final Office Action mailed Jan. 7, 2009", 5 pgs.

"U.S. Appl. No. 11/077,583, Final Office Action mailed Jul. 22, 2009", 9 Pgs.

"U.S. Appl. No. 11/077,583, Advisory Action mailed Oct. 29, 2009", 3 pgs.

"U.S. Appl. No. 11/077,583, Notice of Allowance mailed Mar. 25, 2010", 4 Pgs.

"U.S. Appl. No. 11/077,583, Response filed May 7, 2009 to Non Final Office Action mailed Jan. 7, 2009", 13 pgs.

"U.S. Appl. No. 11/077,583, Response filed Oct. 22, 2009 to Final Office Action mailed Jul. 22, 2009", 11 pgs.

"U.S. Appl. No. 11/077,583, Final Office Action mailed Oct. 6, 2008", 8 pgs.

"European Application Serial No. 06737115.3, Office Action mailed Aug. 20, 2008", 3 pgs.

"European Application Serial No. 06737115.3, Response filed Feb. 26, 2009 to Office Action mailed Aug. 20, 2008", 17 pgs.

"International Search Report and Written Opinion for Application No. PCT/US2006/007897, Date Mailed Aug. 11, 2006", 14 Pages.

Brown, Colin, "Electric shock and the human body", *Phys. Educ. 21. 1986*, pp. 350-353., (1986), 350-353.

Chiou, C. W, et al., "Efferent vagal innervation of the canine atria and sinus and atrioventricular nodes. The third fat pad.", *Circulation*, 95(11), (Jun. 3, 1997), 2573-84.

Dickerson, L. W, et al., "Parasympathetic neurons in the cranial medial ventricular fat pad on the dog heart selectively decrease venticular contractility", *Journal of the Autonomic nervous systems*; 70(2), (May 28, 1998), 129-141.

Gatti, P J, et al., "Vagal control of left ventricular contractility is selectively mediated by a cranioventricular intracardiac ganglion in the cat", *J Auton Nerv Syst.*, 66(3), (Oct. 13, 1997), 138-44.

Henning, R J, et al., "Vagal stimulation attenuates sympathetic enhancement of left ventricular function", *American Journal of Physiology*, 258(5 Pt 2), (May 1990), H1470-5.

Lathrop, D. A, "On the neural connection", *Journal of Cardiovascular Electrophysiology*, vol. 12, No. 7, (Jul. 2001), 841-844.

Nolan, J., et al., "Prospective Study of Heart Rate Variability and Mortality in Chronic Heart Failure: Results of the United Kingdom Heart Failure Evaluation and Assessment of Risk Trial (UK-Heart).", *Circulation*, 98(15), (1998), 1510-1516.

Schauerte, P. N, et al., "Transvenous parasympathetic cardiac nerve stimulation: an approach for stable sinus rate control", *Journal of Cardiovascular Electrophysiology*, 10(11), (Nov. 1999), 1517-1524.

Schauerte, P., et al., "Transvenous Parasympathetic Nerve Stimulation in the Inferior Vena Cava and Atrioventricular Conduction", *Journal of Cardiovascular Electrophysiology*, 11(1), (Jan. 2000), 64-69.

Sigurdsson, A., et al., "The Role of Neurohormonal Activation in Chronic Heart Failure and Postmyocardial Infarction", *American Heart Journal*, 132(1, Part 2), (Jul. 1996), 229-234.

Takahashi, N, et al., "Vagal modulation of ventricular tachyarrhythmias induced by left ansae subclaviae stimulation in rabbits", *Japanese Heart Journal*, 39(4), (Jul. 1998), 503-11.

Tsuboi, M, "Inotropic, chronotropic, and dromotropic effects mediated via parasympathetic ganglia in the dog heart", *American Journal of Physiology—Heart & Circulatory Physiology*, vol. 279, No. 3, (Sep. 2000), H1201-7.

Vanoli, E., et al., "Vagal Stimulation and Prevention of Sudden Death in Conscious Dogs With a Healed Myocardial Infarction", *Circulation Research*, 68(5), (May 1991), 1471-1481.

Verrier, Richard L, et al., "The Enigmatic Cardiac Fat Pads: Critical but Underappreciated Neural Regulatory Sites", *Journal of Cardiovascular Electrophysiology*, vol. 13, No. 9, (Sep. 2002), 902-903.

Zhou, X, et al., "Prevention of high incidence of neurally mediated ventricular arrhythmias by afferent nerve stimulation in dogs", *Circulation*, 101(7), (Feb. 22, 2000), 819-24.

\* cited by examiner

NEURAL STIMULATION SYSTEM FOR CARDIAC FAT PADS

CROSS REFERENCE TO RELATED APPLICATION

This application is a divisional of U.S. application Ser. No. 11/077,583, filed Mar. 11, 2005 now U.S. Pat. No. 7,769,446, which is hereby incorporated by reference in its entirety.

TECHNICAL FIELD

This application relates generally to medical devices and, more particularly, to systems, devices and methods to provide neural stimulation.

BACKGROUND

The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. Changes in autonomic balance is reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult. Reduced autonomic balance (increase in sympathetic and decrease in parasympathetic cardiac tone) during heart failure has been shown to be associated with left ventricular dysfunction and increased mortality. Research also indicates that increasing parasympathetic tone and reducing sympathetic tone may protect the myocardium from further remodeling and predisposition to fatal arrhythmias following myocardial infarction.

SUMMARY

Various aspects of the present subject matter relate to an implantable medical device. In various embodiments, the device comprises a header, a neural stimulator, a detector and a controller. The header includes at least one port to connect to at least one lead, including a first channel to connect to a first lead electrode for use to provide neural stimulation to a first neural stimulation site for a heart, and a second channel to connect to a second lead electrode for use to provide neural stimulation to a second neural stimulation site for the heart. The neural stimulator is connected to the first channel to selectively apply neural stimulation to the first neural stimulation site for the heart, and is connected to the second channel to selectively apply neural stimulation to the second neural stimulation site for the heart. The detector is connected to the header to receive at least one sensed signal indicative of at least one sensed physiological parameter. The detector is adapted to generate at least one feedback signal based on the at least one sensed signal. The controller is connected to the detector and to the neural stimulator to selectively deliver a neural stimulation therapy based on the feedback signal. The neural stimulation therapy delivers a first therapy signal through the first channel to the first neural stimulation site for the heart to selectively control contractility for the heart. The neural stimulation therapy delivers a second therapy signal through the second channel to the second neural stimulation site for the heart to selectively control one of a sinus rate and an AV conduction for the heart.

In various device embodiments, the first neural stimulation site for the heart includes an SVC-AO cardiac fat pad located proximate to a junction between a superior vena cava and an aorta, and the second neural stimulation site for the heart includes a cardiac fat pad selected from a group of fat pads consisting of a PV cardiac fat pad associated with an sinoatrial (SA) node and an IVC-LA cardiac fat pad associated with an atrioventricular (AV) node. The PV cardiac fat pad is located proximate to a junction between a right atrium and right pulmonary vein. The IVC-LA cardiac fat pad is located proximate to a junction between an inferior vena cava and a left atrium.

Various aspects of the present subject matter relate to a method. In various embodiments, the method comprises providing a feedback signal indicative of at least one physiological signal, and providing a neural stimulation therapy responsive to the feedback signal. In these embodiments, providing the neural stimulation therapy includes stimulating an SVC-AO cardiac fat pad to selectively control contractility for the heart, stimulating a PV cardiac fat pad associated with an sinoatrial (SA) node to selectively control a sinus rate, and stimulating an IVC-LA cardiac fat pad associated with an atrioventricular (AV) node to selectively control AV conduction.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1A:
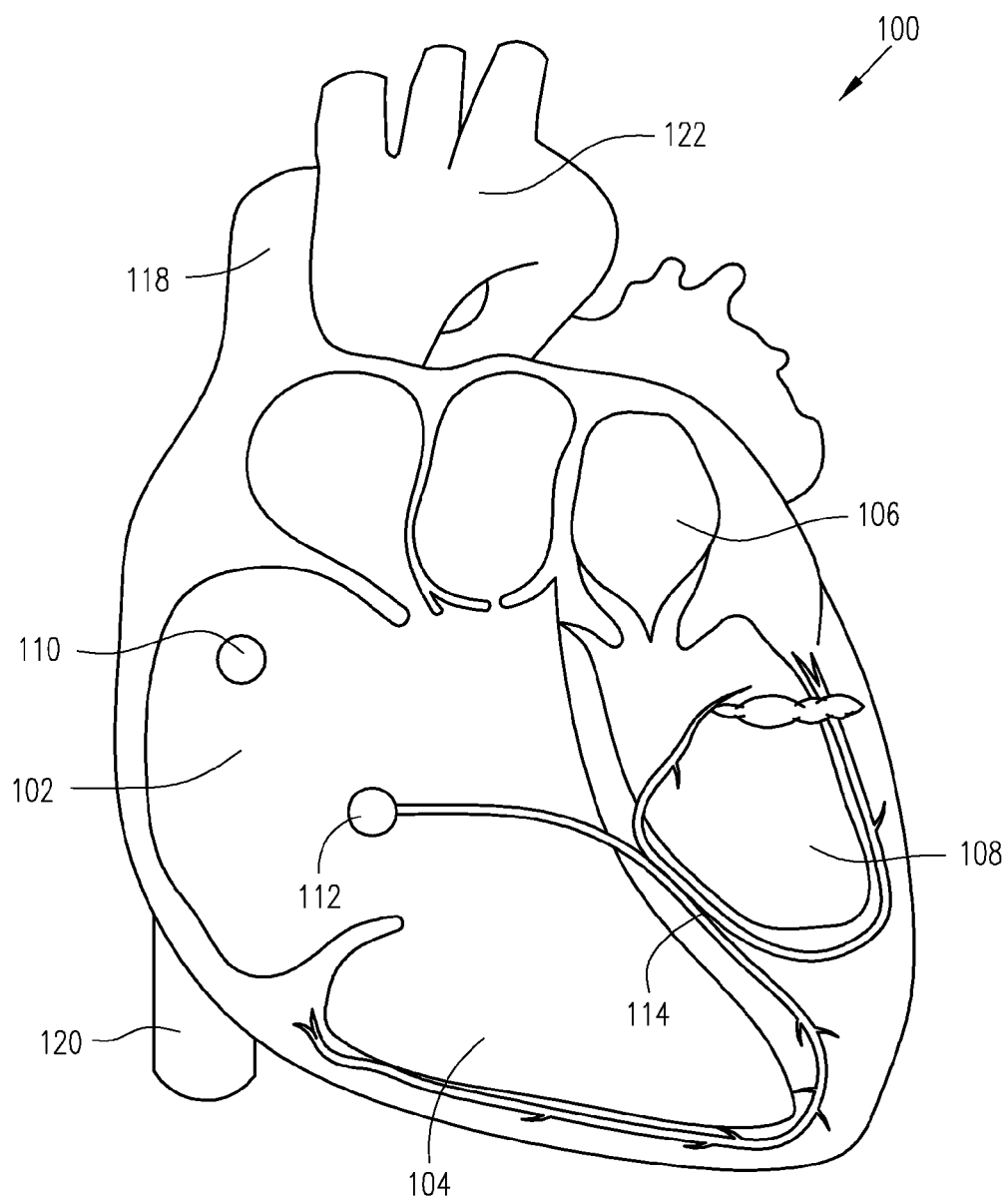
FIGS. 1A-1C illustrate a heart and are useful to illustrate the physiology associated with the electrical stimulation of cardiac fat pads to selectively achieve a specific result, such as a selective chronotropic and/or inotropic result, according to various embodiments of the present subject matter.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. Additionally, the identified embodiments are not necessarily exclusive of each other, as some embodiments may be able to be combined with other embodiments. The following detailed description is, therefore, not to be taken in a limiting sense, and the scope is defined only by the appended claims, along with the full scope of legal equivalents to which such claims are entitled.

Examples of Therapeutic Applications

Some embodiments of the present subject matter provide therapies for situations in which an increase in the amount of sympathetic nerve traffic to the myocardium is needed, such as conditions in which an increase in heart rate or an increase in the inotropic state of the heart is desirable. Examples of such situations include bradycardia and acute cardiac failure. Selective stimulation of autonomic epicardial ganglia can be used to selectively activate the parasympathetic nervous system. Embodiments of the present subject matter decrease left ventricular contractility via postganglionic parasympathetic nervous system activity. Some embodiments of the present subject matter pace the heart to treat of arrhythmias by stimulating the autonomic nerves rather than stimulating the myocardium. Embodiments of the present subject matter pace the heart using the autonomic nervous system to provide chronotropic and inotropic control via selective cardiac neural stimulation. The selective neural stimulation provide a natural stimulus for pacing.

Ischemia, which may occur because of coronary artery disease, can cause increased sympathetic nervous system activity. This increased sympathetic activity can result in increased exposure of the myocardium to epinephrine and norepinephrine. These catecholamines activate intracellular pathways within the myocytes, which lead to myocardial death and fibrosis. Stimulation of the parasympathetic nerves inhibits the effect from the ischemia-induced increase in sympathetic activity.

Embodiments of the present subject matter selectively stimulate vagal cardial nerves following a myocardial infarction or in heart failure patients, thus providing a treatment to protect the myocardium from further remodeling and arrhythmogenesis. Embodiments of the present subject matter selectively stimulate cardiac sympathetic nervous system activity to treat bradycardia or to treat conditions where increasing the inotropic state of the myocardium is beneficial such as sudden cardiac failure, for example.

The intrinsic cardiac ganglionated plexus integrate and process afferent and efferent autonomic nervous system activity. Embodiments of the present subject matter stimulation of these pathways to fine-tune autonomic balance to mitigate a number of cardiovascular disorders. Some embodiments provide selective neural stimulation to increase vagal tone to reduce myocardial exposure to epinephrine, thus reducing myocardial death and fibrosis. Some embodiments provide selective neural stimulation to increase vagal tone to prevent post-MI patients form further remodeling or predisposition to fatal arrhythmias. Some embodiments provide selective neural stimulation to provide autonomic balance following ischemic insult to prevent the onset of lethal arrhythmias. Some embodiments provide selective neural stimulation to provide specific cardiac pacing effects based on the stimulated fat pad. The selective neural stimulation provides a means for precisely altering autonomic tone to cardiac tissue while sparing extracardiac effects, such as can occur from stimulation of the vagus nerve trunk. Thus, the present subject matter provides means for altering autonomic tone to specific areas of the heart (e.g. left ventricular contractility).

Examples of Therapeutic Systems

An implantable stimulating electrode is placed near intrinsic autonomic cardiac nerves and ganglia. Some embodiments use epicardial leads for epicardial stimulation of a target neural stimulation site, some embodiments use intravascular leads for transvascular neural stimulation of a target neural stimulation site, and some embodiments use intravascular leads adapted to puncture a vessel for percutaneous stimulation of a target neural stimulation site. An implantable pulse generator with programmable pulse generating features is attached to the electrode. Electrical activation of the electrode(s) stimulates the target sympathetic or parasympathetic nerves anatomically located near the electrode(s) at a strength and frequency sufficient to elicit depolarization of the adjacent nerve(s) while sparing the underlying myocardium.

Some embodiments electrically stimulate autonomic nerves innervating the myocardium without eliciting depolarization and contraction of the myocardium directly because the threshold for neural depolarization (especially myelinated vagal nerve fibers of the parasympathetic nervous system) is much lower than that of myocardial tissue. Differing frequencies of stimulation can be used so as to depolarize post (or pre in case of vagal nerve stimulation) ganglionic nerve fibers. A stimulus response curve may be generated to determine the minimal threshold required to elicit myocardial contraction, and still maintain neural depolarization of the site. Some embodiments time the neural stimulation with the refractory period.

Stimulation can be combined with sensor technology, and may occur during combinations of pacing parameters to get selective effects. Some embodiments adjust parameters of the neural stimulation to elicit selective effects. For example, the strength of the parasympathetic response can be modulated by adjusting the amplitude of a neural stimulation signal. However, judicious selection of stimulation frequency can either activate the parasympathetic pathway or block the baseline level of parasympathetic activity, causing the opposite physiological effect. The neural stimulation can be applied during cardiac pacing to elicit selective effects. For example, if contractility modulation is desired, fat pad stimulation can be applied during pacing to achieve contractility effects without rate effects.

Some embodiments stimulate an SVC-AO cardiac fat pad located proximate to a junction between a superior vena cava and an aorta. Stimulation of the SVC-AO fat pad specifically reduces the contractility of the left ventricle, thus providing a neural stimulation treatment for diseases such as heart failure and/or post myocardial infarction remodeling. Some embodiments stimulate a PV cardiac fat pad associated with an sinoatrial (SA) node and some embodiments stimulate an IVC-LA cardiac fat pad associated with an atrioventricular (AV) node. The PV cardiac fat pad is located proximate to a junction between a right atrium and right pulmonary vein, and the IVC-LA cardiac fat pad is located proximate to a junction between an inferior vena cava and a left atrium. Stimulation of the PV cardiac fat pad reduces a sinus rate, and stimulation of the IVC-LA fat pad increases AV conduction, which affects timing between a contractions in a right atrium and contractions in the right ventricle. Fat pad stimulation activates parasympathetic efferents. Because fat pad ganglia form part of the efferent pathway, stimulation of cardiac fat pads directly effects cardiac tissue. For example, stimulating the parasympathetic efferents can selectively affect rate, and conduction. Stimulation of the parasympathetic also has post-ganglionic inhibition of sympathetic outflow.

Leads are used to deliver the selective neural stimulation to a cardiac neural stimulation site. Lead embodiments include epicardial leads and intravascularly-fed leads. Various lead embodiments are designed and positioned to provide multiple effects, sensing, pacing ICD etc. in addition to neural stimulation. The present subject matter uses an epicardial, transvascular and/or percutaneous approaches to elicit adjacent neural depolarization, thus avoiding direct neural contact with a stimulating electrode and reducing problems associated with neural inflammation and injury associated with direct contact electrodes.

Autonomic Nervous System

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Stimulating the sympathetic and parasympathetic nervous systems can have a number of physiological effects. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems. To avoided these undesired effects, embodiments of the present subject matter provide neural stimulation to cardiac nerves to selectively achieve a specific result.

Cardiac Physiology

Figure 1B:
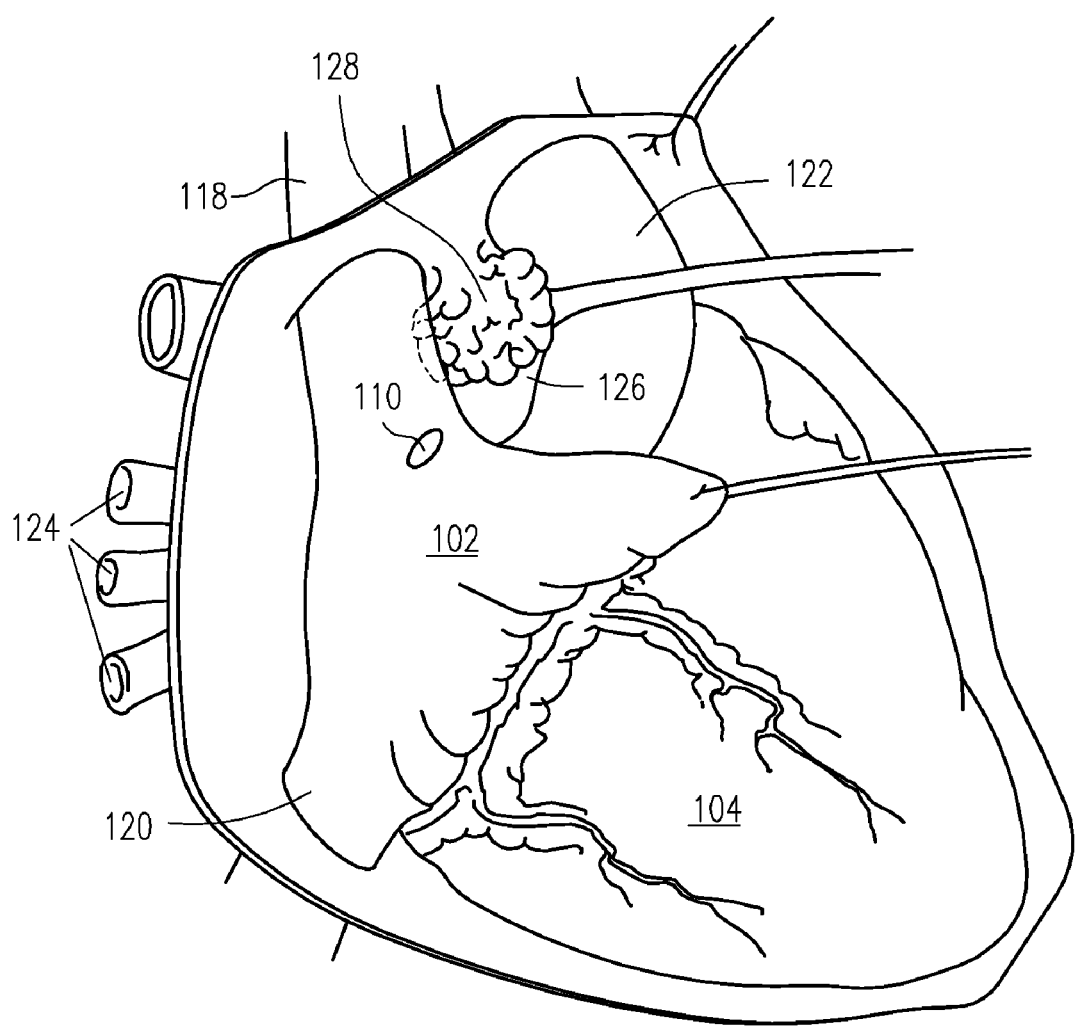
Figure 1C:
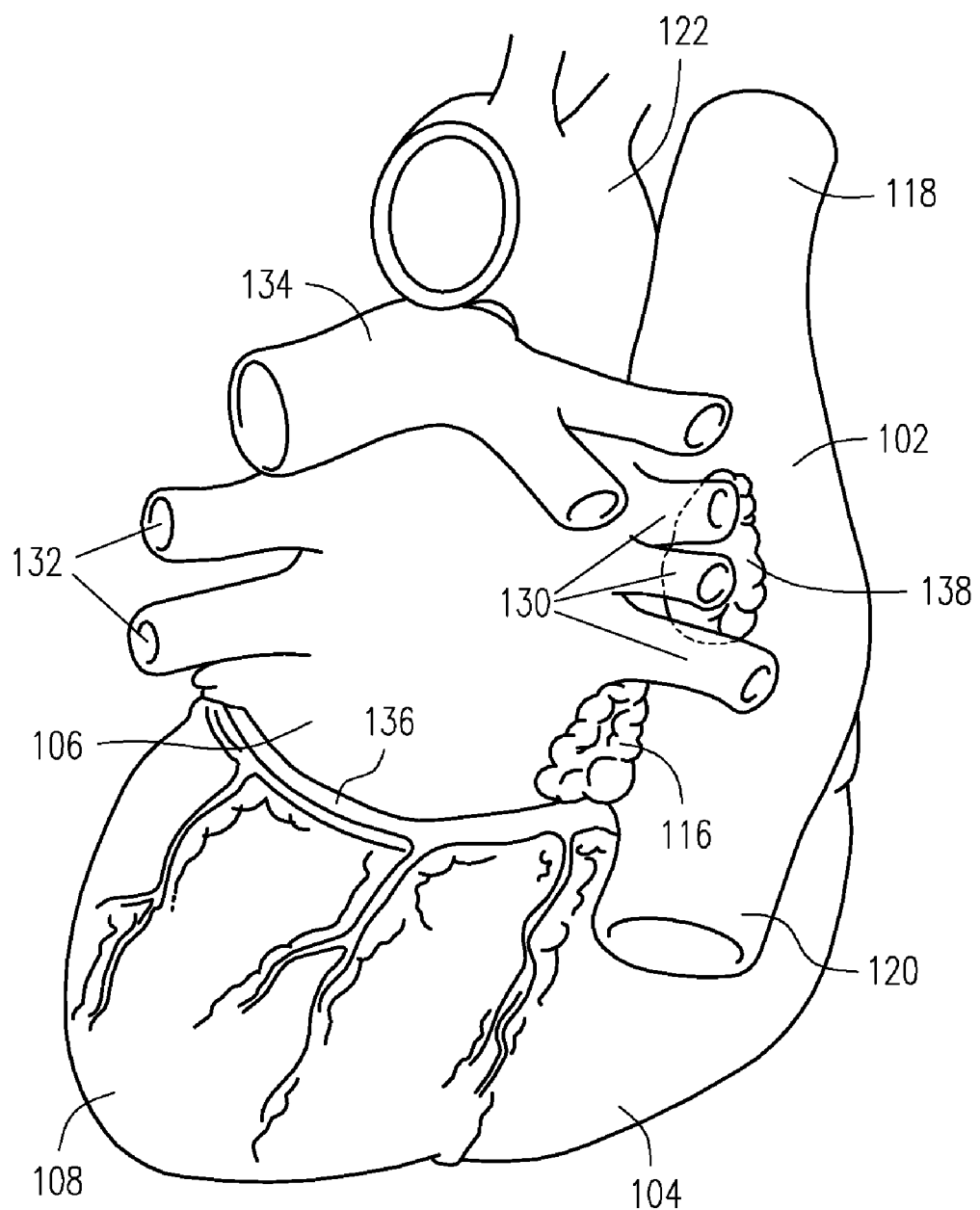

FIGS. 1A-1C illustrate a heart and are useful to illustrate the physiology associated with the electrical stimulation of cardiac fat pads to selectively achieve a specific result, such as a selective chronotropic and/or inotropic result, according to embodiments of the present subject matter. The illustrated heart 100 includes a right atrium 102, a right ventricle 104, a left atrium 106 and a left ventricle 108. The illustrated heart 100 also includes a sinoatrial (SA) node 110 and an atrioventricular (AV) node 112. FIG. 1A illustrates the cardiac conduction system which controls heart rate. This system generates electrical impulses and conducts them throughout the muscle of the heart to stimulate the heart to contract and pump blood. The cardiac conduction system includes the SA node 110 and the AV node 112. The autonomic nervous system controls the firing of the SA node to trigger the start of the cardiac cycle. The SA node includes a cluster of cells in the right atrium that generates the electrical impulses. The electrical signal generated by the SA node moves from cell to cell down through the heart until it reaches the AV node 112, a cluster of cells situated in the center of the heart between the atria and ventricles. The AV node functions as an electrical relay station between the atria and the ventricles, such that electrical signals from the atria must pass through the AV node to reach the ventricles. The AV node slows the electrical current before the signal is permitted to pass down through to the ventricles, such that the atria are able to fully contract before the ventricles are stimulated. After passing the AV node, the electrical current travels to the ventricles along special fibers 114 embedded in the walls of the lower part of the heart.

FIGS. 1B and 1C illustrate other views a heart, including epicardial fat pads that function as target cardiac neural stimulation sites. FIGS. 1B and 1C illustrate the right side and left side of the heart, respectively.

FIG. 1B illustrates the right atrium 102, right ventricle 104, SA node 110, superior vena cava 118, inferior vena cava 120, aorta 122, right pulmonary veins 124, and right pulmonary artery 126. FIG. 1B also illustrates a cardiac fat pad 128, referred to herein as the SVC-AO fat pad, between the superior vena cava and aorta. Nerve endings in the SVC-AO cardiac fat pad 128 are stimulated in some embodiments using an electrode screwed into or otherwise placed in the fat pad, and are stimulated in some embodiments using an intravenously-fed lead proximately positioned to the fat pad in a vessel such as the right pulmonary artery 126 or superior vena cava 118, for example. Some embodiments use an intravascularly-fed lead adapted to puncture through a vessel wall to place an electrode proximate to a target neural stimulation site. An example of such a lead is provided in U.S. patent application Ser. No. 11/077,970, filed on Mar. 11, 2005, which is herein incorporated by reference in its entirety.

FIG. 1C illustrates the left atrium 106, left ventricle 108, right atrium 102, right ventricle 104, superior vena cava 118, inferior vena cava 120, aorta 122, right pulmonary veins 130, left pulmonary vein 132, right pulmonary artery 134, and coronary sinus 136. FIG. 1C also illustrates a cardiac fat pad 138, referred to herein as the PV fat pad, located proximate to a junction between the right atrium and right pulmonary veins and a cardiac fat pad 116, referred to herein as the IVC-LA fat pad, located proximate to or at the junction of the inferior vena cava and left atrium. Nerve endings in the PV fat pad 138 are stimulated in some embodiments using an electrode screwed into the fat pad 138, and are stimulated in some embodiments using an intravenously-fed lead proximately positioned to the fat pad in a vessel such as the right pulmonary artery 134 or right pulmonary vein 130, for example.

Some embodiments use an intravascularly-fed lead adapted to puncture through a vessel wall to place an electrode proximate to a target neural stimulation site.

FIG. 1C also illustrates a cardiac fat pad 116, referred to herein as the IVC-LA fat pad, located proximate to a junction between the inferior vena cava 120 and the left atrium 106. Nerve endings in the IVC-LA fat pad 116 are stimulated in some embodiments using an electrode screwed into the fat pad using either an epicardial or intravascular lead, and are transvascularly stimulated in some embodiments using an intravascular electrode proximately positioned to the fat pad in a vessel such as the inferior vena cava 120 or coronary sinus 136 or a lead in the left atrium 106, for example. Some embodiments use an intravascularly-fed lead adapted to puncture through a vessel wall to place an electrode proximate to a target neural stimulation site.

The function of the SVC-AO fat pad, positioned between the medial superior vena cava and aortic root superior to the right pulmonary artery, has been identified as a "head station" of vagal fibers projecting to both atria and to the IVC-LA and PV fat pads.

The nervous system regulating the rhythm of the heart includes a number of ganglionated fat pads. Parasympathetic ganglia in these discrete epicardial fat pads exert important effects on chronotropy, dromotropy and inotropy.

The PV fat pad is associated with the SA node, and the IVC-LA fat pad is associated with the AV node. Stimulation of the PV fat pad associated with the SA node provides direct vagal inhibition of the SA node, resulting in slowing of the sinus rate without prolonging AV conduction time. The IVC-LA fat pad selectively innervates the AV nodal region and regulates AV conduction. Stimulation of the IVC-LA fat pad extends the AV conduction time without slowing of the sinus rate.

Disruption of neural activity in the fat pads can cause significant heterogeneity of repolarization, and tend to result in atrial arrhythmias. An intrinsic cardiac neuronal network is important to both intracardiac and extracardiac integration of autonomic control of cardiac function. Unfortunately, this cardiac neuronal network can be damaged, thus adversely affecting the autonomic balance.

Myocardial ischemia can compromise the function of cardiac intrinsic neurons embedded with the fat pads, potentially inducing arrhythmias. Diabetic neuropathy affecting intrinsic cardiac innervation can also enhance susceptibility to arrhythmias. Surgery and ablation procedures may sever or otherwise damage a portion of the cardiac neuronal network, thus damaging heart rhythm control.

Cardiac performance depends on heart rate, preload, afterload and contractility. The following provides one representation for cardiac performance:

Cardiac Output=Heart Rate×Stroke Volume

Stroke volume depends on preload, the left ventricular end diastolic volume related to the amount of stretch in the left ventricle stretch. Stroke volume also depends on afterload, the total peripheral resistance. Contractility relates to the ability of the heart muscle to shorten which relates to the ability of the myocardium to respond to preload and afterload. Increased contractility has a positive inotropic effect, being associated with increased stroke volume and ejection fraction. Decreased contractility is associated with decreased stroke volume and ejection fraction. Contractility is increased by sympathetic discharge to the ventricles, circulating epinephrine, and faster heart rates. Cardiac performance may be defined by a number of different parameters that tend to be interrelated to some degree. Performance parameters include, but are not limited to, stroke volume, stroke work, rate of shortening for the muscle fibers, cardiac output and ejection fraction. Thus, a number of sensors can be used to provide either a direct or indirect indicator of contractility. Ejection fraction relates to the portion of blood that is pumped out of a filled ventricle as a result of a heartbeat. The heart normally pumps out or ejects about two-thirds of the blood with each beat. The ejection fraction is an indicator of the heart's health. If the heart is diseased from a heart attack or another cardiac condition, the ejection fraction may fall, for example, to a third.

Cardiac rate, AV conduction, and contractility are mediated through ganglia located in cardiac fat pads. Data indicates that specific ganglia selectively mediates cardiac rate, AV conduction, and contractility. Sympathetic neural stimulation directly increases contractility, indirectly increases preload and afterload. Embodiments of the present subject provide specific cardiac neural stimulation to achieve a desired local effect, such as increasing ventricular contractility without increasing heart rate or inducing an arrhythmia, for example. Embodiments of the present subject matter selectively stimulate cardiac fat pads to selectively control contractility for the heart, sinus rate and AV conduction. Embodiments of the present subject matter control the stimulation with feedback signals indicative of contractility, sinus rate and/or AV conduction.

Examples of sensors that are capable of providing a feedback signal capable of being indicative of cardiac contractility include sensors to directly measure or sense contractility, and sensors to indirectly measure or sense contractility. An example of a sensor to directly measure contractility is a strain gauge. An example of a sensor to indirectly measure contractility is a sensor to measure cardiac output.

Examples of sensors that are capable of providing a feedback signal capable of being indicative of a sinus rate include electrode(s) positioned proximate to the sinoatrial (SA) node and cooperating sensing circuitry connected to the electrode(s) to detect intrinsic events near the SA node. Rate can be sensed using electrograms, leadless ECG electrodes on the can of the implantable device, flow sensors, and heart sounds using a vibration sensor/accelerometer, for example.

Examples of sensors that are capable of providing a feedback signal capable of being indicative of an atrioventricular (AV) conduction include an electrode positioned in or proximate to a right atrium, an electrode positioned in or proximate to a right ventricle, and cooperating sensing circuitry connected to the electrodes to detect intrinsic events on each side of the AV node. AV conduction can be sensed using dual chamber electrograms, leadless ECG electrodes on the can of the implantable device, and heart sounds, which may be used to detect AV dyssynchrony.

Implantable Medical Device Embodiments

Implantable cardiac devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. AV conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the SA node to the atrial myocardium, to the AV node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified AV delay interval with respect to the detection of an intrinsic atrial contraction or delivery of an atrial pace.

Embodiments of the present subject matter provide selective cardiac neural stimulation to pace the heart, improve contractility and thus provide a natural stimulus to improve pumping efficiency and cardiac output. For example, the PV fat pad is stimulated to control sinus rate, the IVC-LA fat pad is stimulated to control AV conduction, and the SVC-AO fat pad is stimulated to control contractility.

Figure 2:
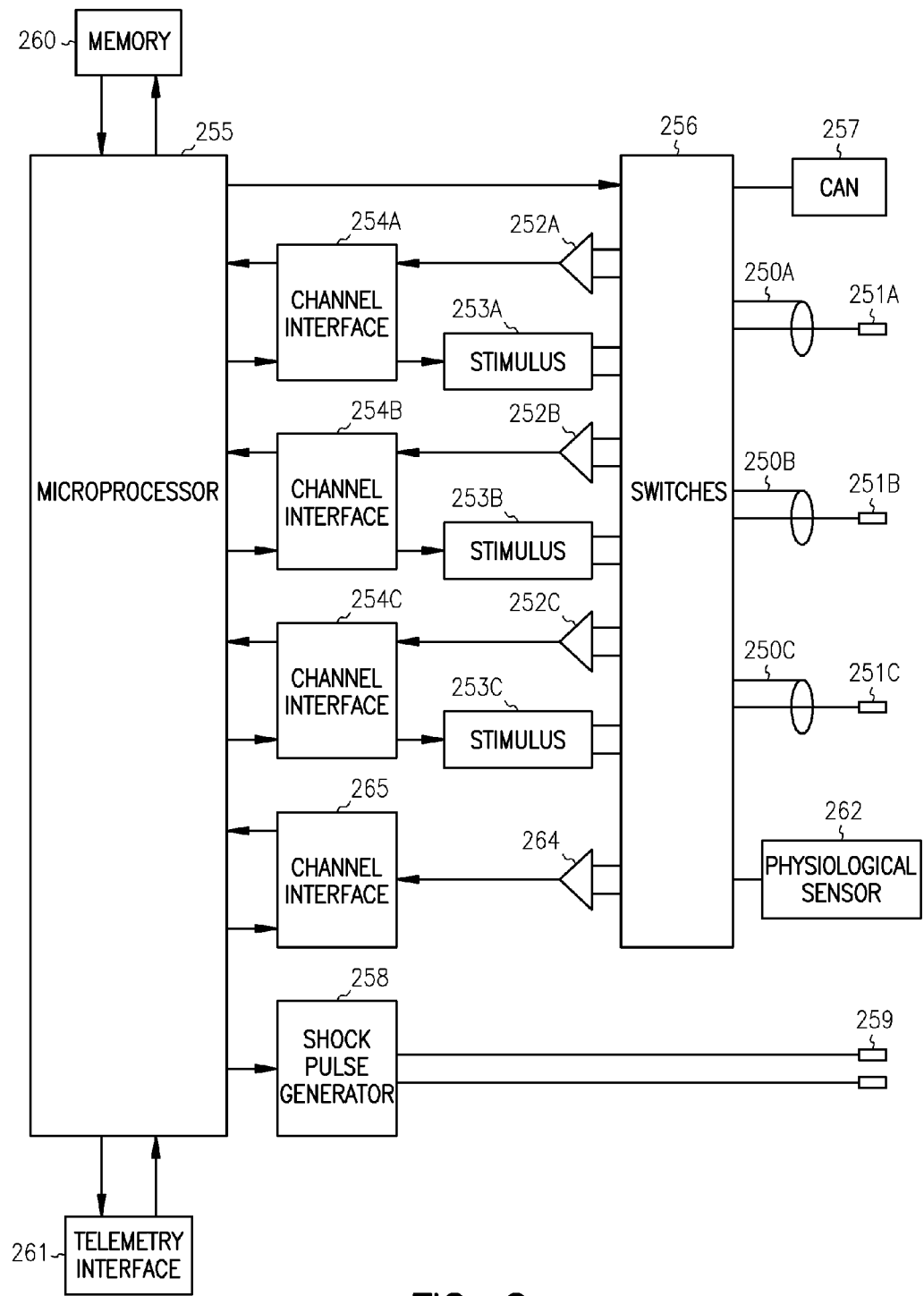
FIG. 2 illustrates a system diagram of an implantable medical device embodiment configured for multi-site stimulation and sensing, according to various embodiments of the present subject matter.

FIG. 2 illustrates a system diagram of an implantable medical device embodiment configured for multi-site stimulation and sensing. Pacing, as used in the discussion of this figure, relates to electrical stimulation. In various embodiments, the stimulation for a given channel includes stimulation to capture myocardia, neural stimulation or both pacing and neural stimulation. Three exemplary sensing and pacing channels designated "A" through "C" comprise bipolar leads with ring electrodes 250A-C and tip electrodes 251A-C, sensing amplifiers 252A-C, pulse generators 253A-C, and channel interfaces 254A-C. Each of these channels thus includes a stimulation channel extending between the pulse generator, the electrode and a sensing channel extending between the sense amplifier and the electrode. The channel interfaces 254A-C communicate bidirectionally with microprocessor 255, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry detects a chamber sense, either an atrial sense or ventricular sense, when an electrogram signal (i.e., a voltage sensed by an electrode representing cardiac electrical activity) generated by a particular channel exceeds a specified detection threshold. Algorithms used in particular stimulation modes employ such senses to trigger or inhibit stimulation, and the intrinsic atrial and/or ventricular rates can be detected by measuring the time intervals between atrial and ventricular senses, respectively. The AV conduction can be measured by measuring a time interval between atrial and ventricular intrinsic events. According to various embodiments, the pulse generator is adapted to vary parameters of a neural stimulation signal, such as amplitude, frequency and duty cycle, for example.

The switching network 256 is used to switch the electrodes to the input of a sense amplifier in order to detect intrinsic cardiac activity and to the output of a pulse generator in order to deliver stimulation. The switching network also enables the device to sense or stimulate either in a bipolar mode using both the ring and tip electrodes of a lead or in a unipolar mode using only one of the electrodes of the lead with the device housing or can 257 serving as a ground electrode or another electrode on another lead serving as the ground electrode. A shock pulse generator 258 is also interfaced to the controller for delivering a defibrillation shock via a pair of shock electrodes 259 to the atria or ventricles upon detection of a shockable tachyarrhythmia. Channel interface 265 and sense amplifier 264 provide a connection between the microprocessor and the switch to receive a sensed signal from physiological sensor 262 for use as a feedback control signal indicative of the efficacy of the stimulation therapy. Various embodiments sense physiological parameters associated with sinus rate, AV conduction and/or contractility. Examples of sensors to provide such a feedback include, but are not limited to, sensors to detect heart rate, sensors to detect blood pressure, sensors to detect blood flow, sensors to detect respiration and sensors to detect cardiac output.

The controller or microprocessor controls the overall operation of the device in accordance with programmed instructions stored in memory 260, including controlling the delivery of stimulation via the channels, interpreting sense signals received from the sensing channels, and implementing timers for defining escape intervals and sensory refractory periods. The controller is capable of operating the device in a number of programmed stimulation modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited stimulation modes utilize escape intervals to control pacing in accordance with sensed intrinsic activity such that a stimulation pulse is delivered to a heart chamber during a cardiac cycle only after expiration of a defined escape interval during which no intrinsic beat by the chamber is detected. Escape intervals for ventricular stimulation can be restarted by ventricular or atrial events, the latter allowing the pacing to track intrinsic atrial beats. A telemetry interface 261 is also provided which enables the controller to communicate with an external programmer or remote monitor. Some embodiments incorporate sensor channels into the device for receiving signals indicative of sense physiological parameters, such as parameters indicative of contractility, AV conduction and/or sinus rate.

Figure 3:
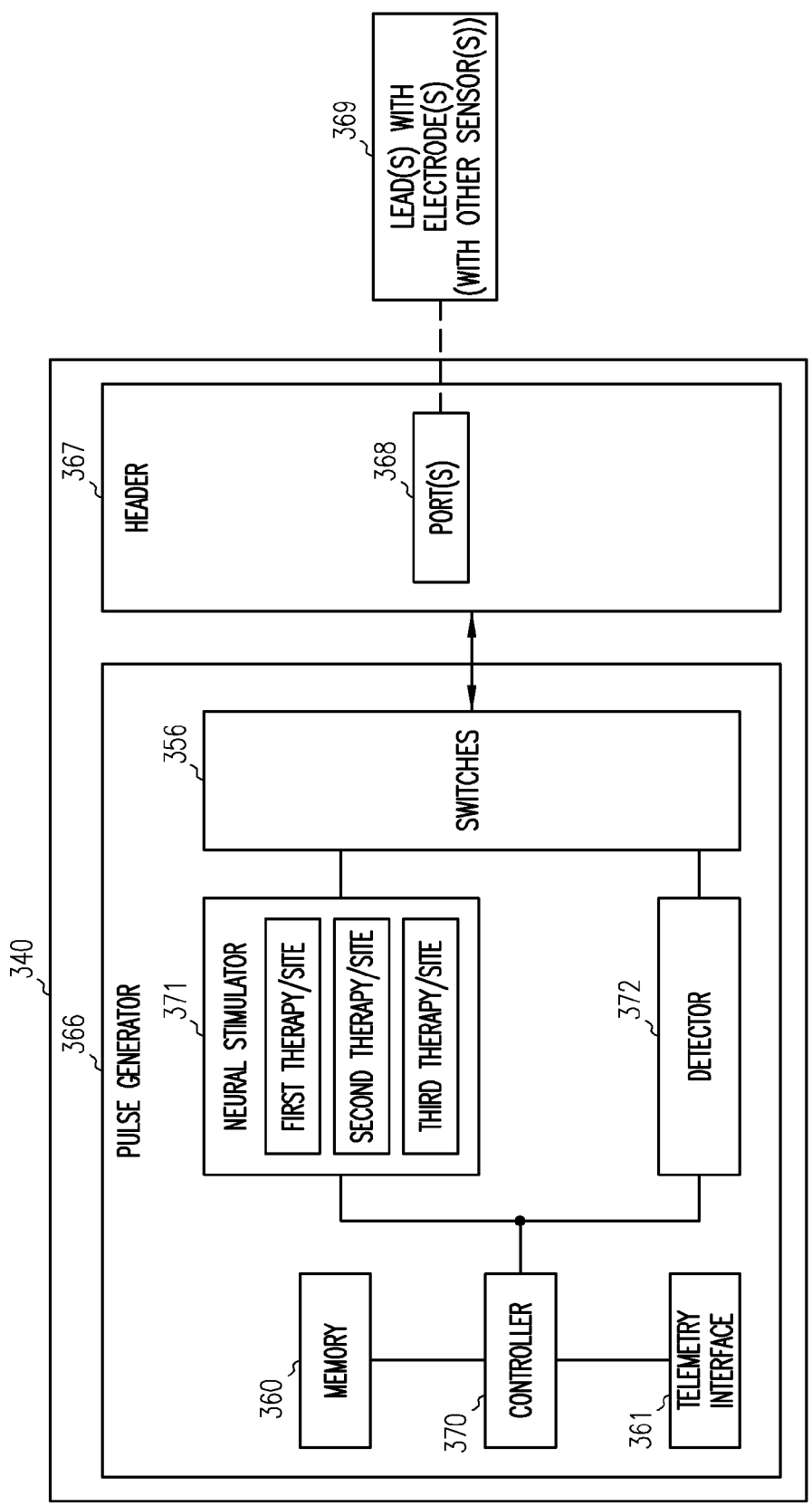
FIGS. 3 and 4 schematically illustrates various embodiments of an implantable medical device used to selectively apply cardiac neural stimulation, according to various embodiments of the present subject matter.
Figure 4:
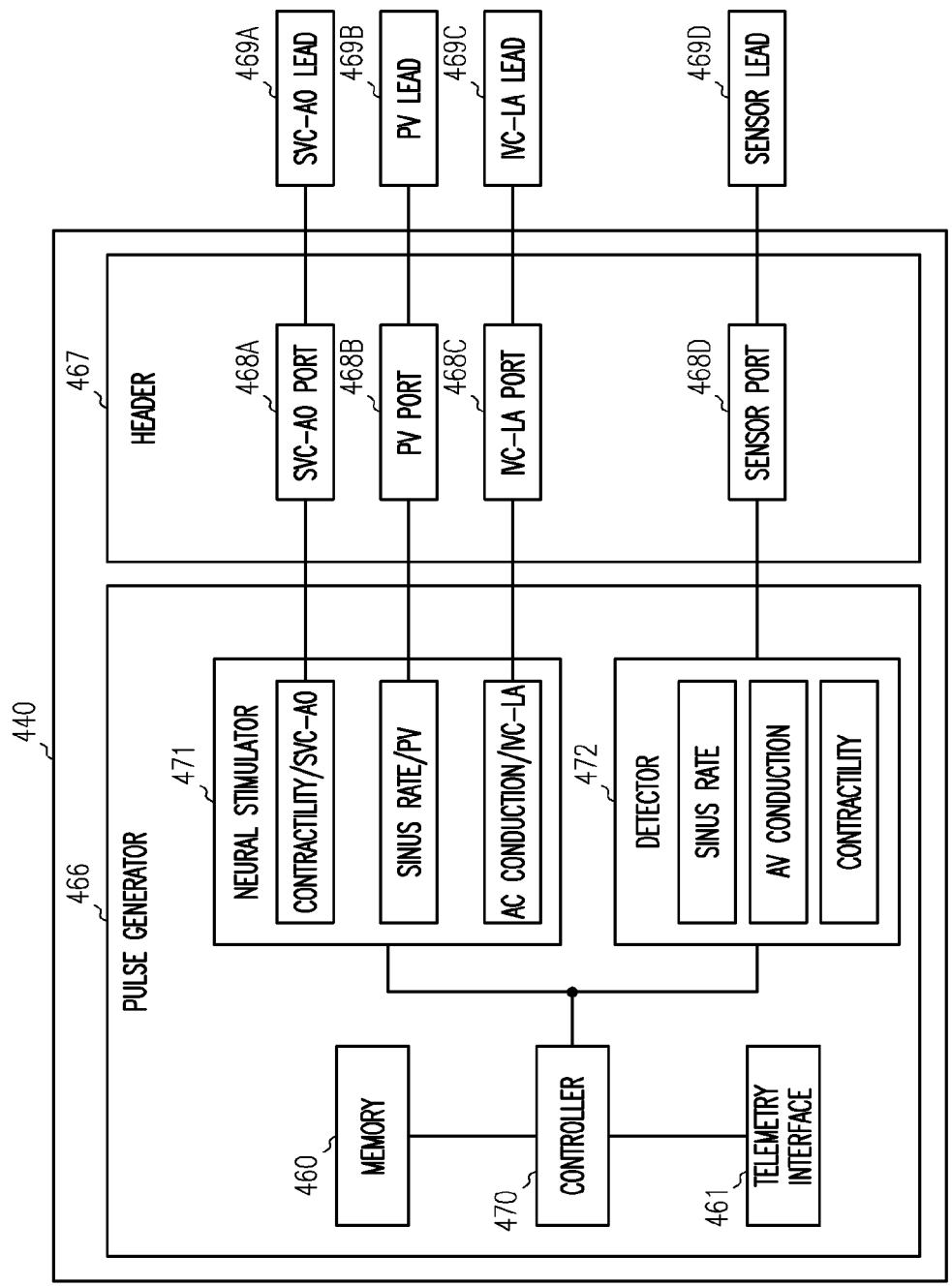

FIGS. 3 and 4 schematically illustrates various embodiments of an implantable medical device used to selectively apply cardiac neural stimulation. The illustrated medical devices of FIGS. 4A-4B include channels, as generally illustrated in FIG. 3, but are illustrated with functional blocks to further illustrate the present subject matter.

FIG. 3 illustrates an implantable medical device. The illustrated device 340 includes a pulse generator 366 and a header 367. The header 367 includes at least one port 368 to receive at least one lead 369 that has at least one electrode. In some embodiments, the lead includes a sensor to detect physiological parameters other than intrinsic electrical signals sensed by electrodes. The header 367 functions as an interface between the lead(s) 369 and the pulse generator 366. The illustrated pulse generator includes a controller 370 connected to a memory 360 and a telemetry interface 361 to communicate with an external programmer. The controller 370 is connected to a neural stimulator 371 and a detector 372. The neural stimulator is adapted to provide a first neural stimulation therapy at a first cardiac neural stimulation site, a second neural stimulation therapy at a second cardiac neural stimulation site, and a third neural stimulation therapy at a third cardiac neural stimulation site. The detector 372 is adapted to receive a signal indicative of physiological parameter or parameters, and provide a feedback signal to the controller 370 based on the received signal. Examples of sensed physiological parameters include, but are not limited to, heart rate, blood pressure, blood flow, respiration and cardiac output.

The circuits or modules 371 and 372 appropriately interface with the electrode(s), and in some embodiments other sensors, on the lead(s) via switches 356 (e.g. MOS switches). The switches provide logical connections that allow circuits 371 and 372 to connect to a desired port 368 to access a desired channel on a desired lead. FIG. 3 illustrates circuits 371 and 372 distinct from controller 370. As will be understood by those of ordinary skill in the art upon reading and comprehending this disclosure, various functions associated with circuits 371 and 372 can be integrated with controller 370 in various embodiments.

FIG. 4 illustrates an implantable medical device. The device of FIG. 4 generally corresponds to the device in FIG. 3, adding further detail according to an embodiment of the present subject matter. For the sake of clarity, FIG. 4 illustrates connections between circuits 471 and 472 to ports 468A, 468B, 468C and 468D. The illustrated device 440 includes a pulse generator 466 and a header 467.

The illustrated header 467 incudes an SVC-AO port 468A to receive an SVC-AO lead 469A with at least one electrode to stimulate the SVC-AO fat pad. The illustrated header 467 further includes a PV port 468B to receive a PV lead 469B with at least one electrode to stimulate the PV fat pad. The illustrated header 467 further includes an IVC-LA port 468C to receive an IVC-LA lead 469C with at least one electrode to stimulate the IVC-LA fat pad. The illustrated header 467 further includes a sensor port 468D to receive sensor lead 469D with at least one sensor to sense a physiological signal indicative of the efficacy of the neural therapy to provide closed loop feedback control. The leads 469A, 469B, and 469C can be epicardial leads, intravascular leads for transvascular stimulation of a neural stimulation site outside of the vessel, or intravascular leads for puncturing a vessel for placement of an electrode(s) proximate to a neural stimulation site outside of the vessel. Additionally, a lead can be designed to combine functions associated with two or more leads into one lead.

The header 467 functions as an interface between the lead(s) and the pulse generator 466. The illustrated pulse generator includes a controller 470 connected to a memory 460 and a telemetry interface 461 to communicate with an external programmer. The controller 470 is connected to a neural stimulator 471 and a detector 472. The neural stimulator is adapted to provide a neural stimulation therapy to control contractility by stimulating an SVC-AO fat pad, a neural stimulation therapy to control sinus rate by stimulating a PV fat pad, and a neural stimulation therapy to control AV conduction by stimulating an IVC-LA fat pad. The detector 472 is adapted to receive a signal indicative of physiological parameter or parameters, and provide a feedback signal to the controller 470 based on the received signal. According to various embodiments, the detector 472 is adapted to receive a signal and provide a corresponding feedback signal to the controller that is indicative of a sinus rate, an AV conduction and contractility.

Figure 5:
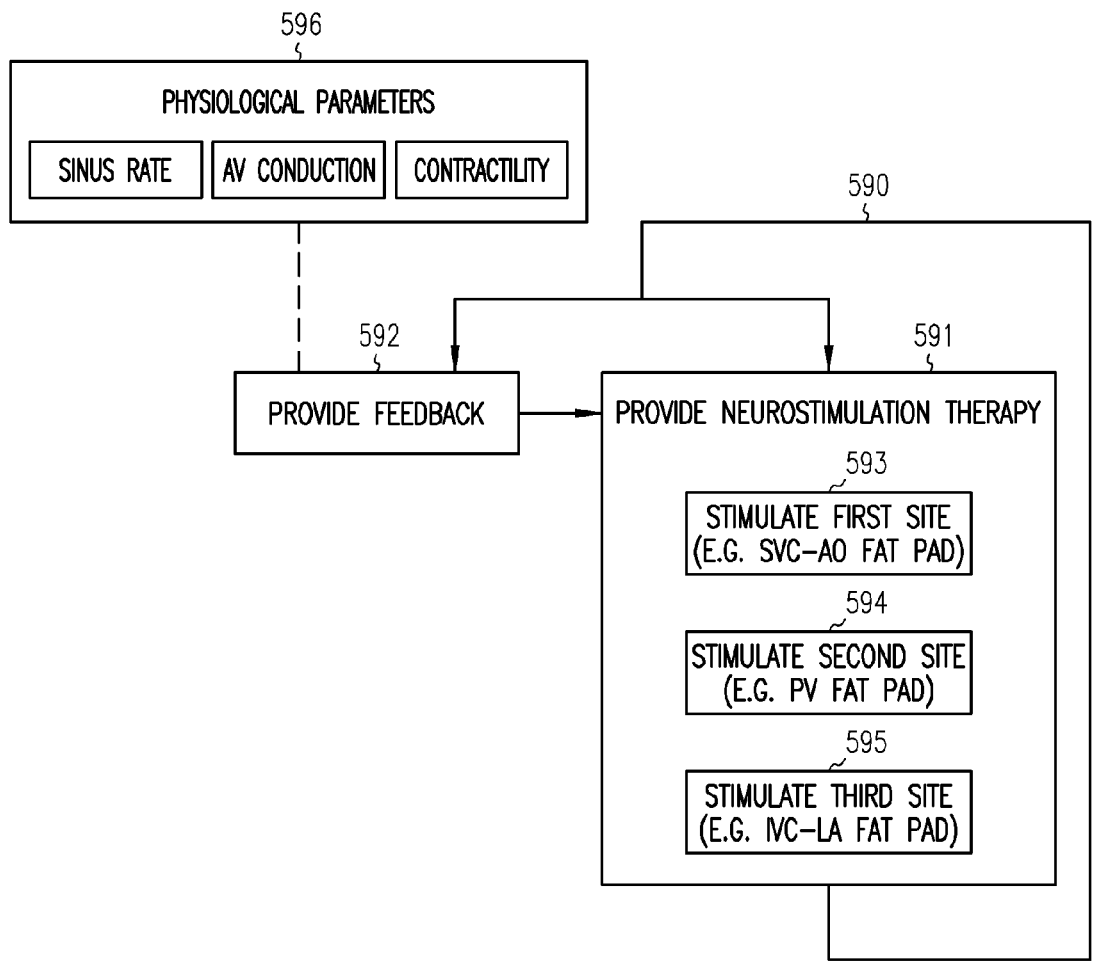
FIG. 5 illustrates a process flow, according to various embodiments of the present subject matter, according to various embodiments of the present subject matter.

FIG. 5 illustrates a process flow, according to various embodiments of the present subject matter. Beginning at 590, the illustrated process provides neural stimulation therapy at 591 and provides feedback at 592 for closed loop control of the neural stimulation therapy. The illustrated neural stimulation therapy includes stimulation of a first site (e.g. 593) and stimulation of a second site (e.g. 594 or 595) to control chronotropic and inotropic parameters. The illustrated neural stimulation therapy also includes a more detailed embodiment in which an SVC-AO cardiac fat pad is stimulated at 593 to selectively control contractility for the heart, a PV cardiac fat pad associated with an sinoatrial (SA) node is stimulated at 594 to selectively control a sinus rate, and an IVC-LA cardiac fat pad associated with an atrioventricular (AV) node is stimulated at 595 to selectively control AV conduction. As illustrated in FIG. 5, the feedback is based on physiological parameters 596 that provide an indication of one or more of the sinus rate, the AV conduction and contractility. In some embodiments, the process flow is stored as computer instructions in memory (e.g. 360 in FIG. 3 and 460 in FIG. 4) and is operated on by the controller (e.g. 370 in FIG. 3 and 470 in FIG. 4) to perform the process.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A method, comprising:
providing a feedback signal indicative of at least one physiological signal; and
providing a neural stimulation therapy responsive to the feedback signal, wherein providing the neural stimulation therapy includes:
stimulating an SVC-AO cardiac fat pad to change ventricular contractility of the heart without changing heart rate or inducing an arrhythmia, the SVC-AO fat pad being located proximate to a junction between a superior vena cava and an aorta; and
stimulating:
a PV cardiac fat pad associated with an sinoatrial (SA) node to change a sinus rate of the heart without changing AV conduction time, the PV cardiac fat pad being located proximate to a junction between a right atrium and right pulmonary veins; or
an IVC-LA cardiac fat pad associated with an atrioventricular (AV) node to change the AV conduction time of the heart without changing the sinus rate, the IVC-LA cardiac fat pad being located proximate to a junction between an inferior vena cava and a left atrium.

2. The method of claim 1, wherein providing a neural stimulation therapy includes using an epicardial lead to epicardially stimulate at least one of the cardiac fat pads.

3. The method of claim 1, wherein providing a neural stimulation therapy includes using an intravascularly-fed lead to transvascularly stimulate at least one of the cardiac fat pads.

4. The method of claim 3, wherein using an intravascularly-fed lead to transvascularly stimulate at least one of the cardiac fat pads includes using a lead configured to be fed into a right pulmonary artery to stimulate the SVC-AO cardiac fat pad.

5. The method of claim 3, wherein using an intravascularly-fed lead to transvascularly stimulate at least one of the cardiac fat pads includes using a lead configured to be fed into the superior vena cava to stimulate the SVC-AO cardiac fat pad.

6. The method of claim 3, wherein using an intravascularly-fed lead to transvascularly stimulate at least one of the cardiac fat pads includes using a lead configured to be fed into the right pulmonary artery to stimulate the PV cardiac fat pad.

7. The method of claim 3, wherein using an intravascularly-fed lead to transvascularly stimulate at least one of the cardiac fat pads includes using a lead configured to be fed into the right pulmonary vein to stimulate the PV cardiac fat pad.

8. The method of claim 3, wherein using an intravascularly-fed lead to transvascularly stimulate at least one of the cardiac fat pads includes using a lead configured to be fed into the interior vena cava to stimulate the IVC-LA cardiac fat pad.

9. The method of claim 3, wherein using an intravascularly-fed lead to transvascularly stimulate at least one of the cardiac fat pads includes using a lead configured to be fed into a coronary sinus to stimulate the IVC-LA cardiac fat pad.

10. The method of claim 3, wherein using an intravascularly-fed lead to transvascularly stimulate at least one of the cardiac fat pads includes using a lead configured to be fed into the left atrium to stimulate the IVC-LA cardiac fat pad.

11. The method of claim 1, wherein providing a feedback signal includes providing a feedback signal indicative of the ventricular contractility.

12. The method of claim 1, wherein the IVC-LA cardiac fat pad associated with the AV node is stimulated, and providing a feedback signal includes providing a feedback signal indicative of the AV conduction time.

13. The method of claim 1, wherein the PV cardiac fat pad associated with the SA node is stimulated, and providing a feedback signal includes providing a feedback signal indicative of the sinus rate.

14. The method of claim 1, wherein providing a neural stimulation therapy includes using neural stimulation to provide specific pacing effects to change:
ventricular contractility of the heart without changing heart rate or inducing an arrhythmia; and
a sinus rate of the heart without changing AV conduction time, or the AV conduction time of the heart without changing the sinus rate.

15. A method, comprising:
providing a feedback signal indicative of at least one physiological signal; and
providing a neural stimulation therapy responsive to the feedback signal, including:
stimulating an SVC-AO cardiac fat pad to change ventricular contractility of the heart without changing heart rate or inducing an arrhythmia, the SVC-AO fat pad being located proximate to a junction between a superior vena cava and an aorta; and
stimulating a PV cardiac fat pad associated with an sinoatrial (SA) node to change a sinus rate of the heart without changing AV conduction time, the PV cardiac fat pad being located proximate to a junction between a right atrium and right pulmonary veins; and
stimulating an IVC-LA cardiac fat pad associated with an atrioventricular (AV) node to change the AV conduction time of the heart without changing the sinus rate, the IVC-LA cardiac fat pad being located proximate to a junction between an inferior vena cava and a left atrium.

16. The method of claim 15, wherein providing a neural stimulation therapy includes using an epicardial lead to epicardially stimulate at least one of the cardiac fat pads.

17. The method of claim 15, wherein providing a neural stimulation therapy includes using an intravascularly-fed lead to transvascularly stimulate at least one of the cardiac fat pads.

18. The method of claim 15, wherein providing a feedback signal indicative of at least one physiological signal includes providing a cardiac rate feedback signal.

19. The method of claim 15, wherein providing a feedback signal indicative of at least one physiological signal includes providing a cardiac rhythm feedback signal.

20. The method of claim 15, wherein providing a feedback signal indicative of at least one physiological signal includes providing a cardiac contractility feedback signal.

21. The method of claim 15, wherein providing a feedback signal indicative of at least one physiological signal includes providing a blood pressure feedback signal.

22. The method of claim 1, wherein providing a neural stimulation therapy includes using neural stimulation to provide specific pacing effects to change ventricular contractility of the heart without changing heart rate or inducing an arrhythmia, change a sinus rate of the heart without changing AV conduction time, and change the AV conduction time of the heart without changing the sinus rate.

23. A method for providing specific pacing effects to a heart, comprising:
changing ventricular contractility of the heart without changing heart rate or inducing an arrhythmia; and changing a sinus rate or an AV conduction time of the heart,
   wherein changing the sinus rate does not change the AV conduction time and changing the AV conduction does not change the sinus rate,
wherein changing the ventricular contractility includes stimulating an SVC-AO cardiac fat pad located proximate to a junction between a superior vena cava and an aorta,
wherein changing the sinus rate includes stimulating a PV cardiac fat pad located proximate to a junction between a right atrium and right pulmonary veins, and
wherein changing the AV conduction time includes stimulating an IVC-LA cardiac fat pad located proximate to a junction between an inferior vena cava and a left atrium.

* * * * *